(12) United States Patent
Ellman et al.

(10) Patent No.: US 6,231,571 B1
(45) Date of Patent: May 15, 2001

(54) ELECTROSURGICAL HANDPIECE FOR TREATING TISSUE

(76) Inventors: Alan G. Ellman; Jon C. Garito, both of 1135 Railroad Ave., Hewlett, NY (US) 11557

( * ) Notice: Subject to any disclaimer, the term of this patent is extended or adjusted under 35 U.S.C. 154(b) by 0 days.

(21) Appl. No.: 09/303,839

(22) Filed: May 3, 1999

(51) Int. Cl.[7] .................................................. A61B 18/18
(52) U.S. Cl. .................................. 606/41; 45/48; 45/49; 45/50; 607/99
(58) Field of Search ................................. 607/96, 98, 99, 607/101, 115, 116; 606/32, 39, 40, 41, 45, 46, 47, 48, 49, 50

(56) References Cited

U.S. PATENT DOCUMENTS

| | | | | |
|---|---|---|---|---|
| 5,275,151 | * | 1/1994 | Shockey et al. | 604/95 |
| 5,441,499 | | 8/1995 | Fritzsch | 606/45 |
| 5,458,597 | * | 10/1995 | Edwards et al. | 606/41 |
| 6,010,500 | * | 1/2000 | Sherman et al. | 606/41 |
| 6,102,046 | * | 8/2000 | Weinstein et al. | 128/898 |

FOREIGN PATENT DOCUMENTS

| | | |
|---|---|---|
| 44 23 216A | 8/1995 | (DE). |
| WO 9622742A | 8/1996 | (EP). |
| WO 97 15238A | 5/1997 | (EP). |

* cited by examiner

*Primary Examiner*—Linda C. M. Dvorak
*Assistant Examiner*—R. Kearney

(57) ABSTRACT

An electrosurgical handpiece that is bipolar or unipolar in operation and that is configured for use in MIS. The bipolar operation confines the electrosurgical currents to a small active region between the active ends of the bipolar electrode and thus reduces the possibility that excessive heat will be developed that can damage patient tissue. The position of the active region can be controlled to avoid patient tissue that may be more sensitive to excessive heat. In one embodiment, the handpiece is constructed with a flexible end controllable by the surgeon so as to allow the surgeon to manipulate the end as desired during the surgical procedure. This feature allows the surgeon to position the active electrode end at the optimum location within, say, a herniated disk to remove undesired regions and to provide controlled heat to shrink the tissue during surgery. In another embodiment, the handpiece is constructed to contain both a bipolar as well as a unipolar electrode, with provision made for selectively operating either of the electrodes. In still another embodiment, a replaceable element for the handpiece comprises scissors.

13 Claims, 8 Drawing Sheets

ELECTROSURGICAL HANDPIECE FOR TREATING TISSUE

This invention relates to an electrosurgical handpiece and an activator for an electrosurgical handpiece.

BACKGROUND OF THE INVENTION

Electrosurgery is a common procedure for dentists, doctors, and veterinarians. Electrosurgical handpieces are commercially available that will accommodate a wide variety of electrode shapes and sizes, such as needles, blades, scalpels, balls and wire loops. Also, multi-function electrodes are available. Electrosurgery has been used for many different kinds of surgical procedures. One surgical procedure involves minimally invasive surgery (MIS), also referred to as laparoscopy, in which a small diameter cannula is inserted via an incision in the patient's body, and a fiber optics viewer (TV camera and monitor) as well as an elongated nozzle from an electrosurgical handpiece are extended through the cannula to the region of the patient where surgery is necessary, and the surgery carried out by the surgeon using the electrosurgical electrode while viewing the procedure through the viewer. Our issued U.S. Pat. No. 5,304,763 describes one form of MIS, the contents of which patent are herein incorporated by reference.

MIS with electrosurgery has also been used for the reduction of herniated disks, by introducing a unipolar electrode via the cannula into the herniated disk region and activating the electrode for the purpose of shrinking the disk. One such system also provides for bending the end of the unipolar electrode in order to position the active end in the desired disk region. In such a procedure, care must be exercised to avoid nerve damage. In the known system, a heat sensor is built into the active unipolar electrode end for the purpose of sensing the heat generated by the electrosurgical currents and shutting off the electrosurgical currents when the heat reaches too high a level.

SUMMARY OF THE INVENTION

An object of the invention is an electrosurgical handpiece that is capable of treating tissue when energized.

Another object of the invention is an electrosurgical handpiece that can be used in MIS and reduces the danger of excessive heat causing possible patient harm.

According to one aspect of the invention, an electrosurgical handpiece is provided that is bipolar in operation and that is configured for use in MIS. The bipolar operation confines the electrosurgical currents to a small active region between the active ends of the bipolar electrode and thus reduces the possibility that excessive heat will be developed that can damage patient tissue. Moreover, the position of the active region can be controlled to avoid patient tissue that may be more sensitive to excessive heat.

In accordance with a preferred embodiment of this aspect of the invention, the handpiece is provided with a dual compartment insulated elongated tube, each of the compartments serving to house one of the two wires of bipolar electrodes.

According to another aspect of the invention, the electrode for MIS use is constructed with a flexible end controllable by the surgeon so as to allow the surgeon to manipulate the end as desired during the surgical procedure. In a preferred embodiment, the flexible end is achieved by weakening at the end the housing for the electrode, and providing a pull string or wire connected to the weakened housing end and with a mechanism at the opposite end for the surgeon to pull the string or wire to flex the housing end to the desired position. This feature allows the surgeon to position the active electrode end at the optimum location within the herniated disk to remove undesired regions and to provide controlled heat to shrink the tissue during surgery.

Still another aspect of the invention is a multi-purpose electrode system adapted for MIS use, which combines both a unipolar and a bipolar electrode. Preferably, the electrodes can be easily interchanged. In a preferred embodiment, the handpiece is provided with a three compartment insulated elongated tube, two of the compartments serving to house one of the two wires of bipolar electrodes, and the third compartment serving to house the wire of an unipolar electrode. Means are provided to selectively extend and operate either the bipolar or unipolar electrode enabling the surgeon, without having to remove the handpiece from the cannula, to successively use the bipolar or unipolar electrode as needed.

In still another aspect of the invention, one of the replaceable elements of the mutipurpose electrode system adapted for MIS use can be a scissors operated either electrically or mechanically.

The construction of the invention will provide important benefits not only for MIS of herniated disks but also for other MIS procedures where controlled electrode position and controlled heat generation is of importance. Such procedures include drying, shrinking, or denaturazing tissue generally and collagen tissue in particular for such purposes as tightening or reducing the tissue.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

DETAILED DESCRIPTION OF THE PREFERRED EMBODIMENTS

The MIS procedures are well known in the art and need no further elaboration here except to state that the invention has to do with the construction of the electrosurgical electrode that is inserted into the cannula during the procedure for the purpose of shrinking or excising tissue. The use of electrosurgical procedures to shrink herniated disks and other tissue is also well known in the art and also needs little elaboration here. It will suffice to state that the procedure with the novel handpiece of the present invention is similar to that using the unipolar electrode with the incorporated heat sensor, except that, with the bipolar handpiece of the invention, no complex temperature sensor and associated control circuit are needed, as, in the case of the bipolar electrode, electrosurgical currents are confined to the small active region between the electrode tips and will cause little if any heat generation at remote tissue locations.

In a preferred embodiment of the invention, an electrode designed for MIS is provided with an outer tubular housing that is stiff enough to be inserted into the cannula and has a straight end portion that is capable of flexure when a bending force is applied but which end portion has inherent memory that will restore the tubular housing to its pre-flexed configuration when the bending force is removed. The tube may be made out of a plastic or a metal such as stainless is steel. Examples of suitable plastics with some flexibility and inherent memory that will keep the tubing straight when the bending flex is removed are Delron, vinyls, and nylon. The location in the tubing where flexure occurs can be established in several ways, the preferred way being to weaken one side of the outer tubing, as for example by spaced slots, at an end region spaced from the tip where flexure is desired. In a preferred embodiment, a handle is provided for supporting the outer tubular housing and the handle is provided with a hand grip and a trigger that is connected to a mechanism to flex the tube end when squeezed. In a preferred embodiment, this result can be obtained by attaching a pull string or wire to the side of the tube that has been weakened by the cutting of slots but beyond the slots. The pull string or wire is attached to the trigger at the opposite end of the tube. When the trigger is squeezed against the grip, the tube end will flex in the direction of the weakened side of the tube. When the trigger is released, the tube due to its inherent memory returns back to its original straight position.

Figure 1:
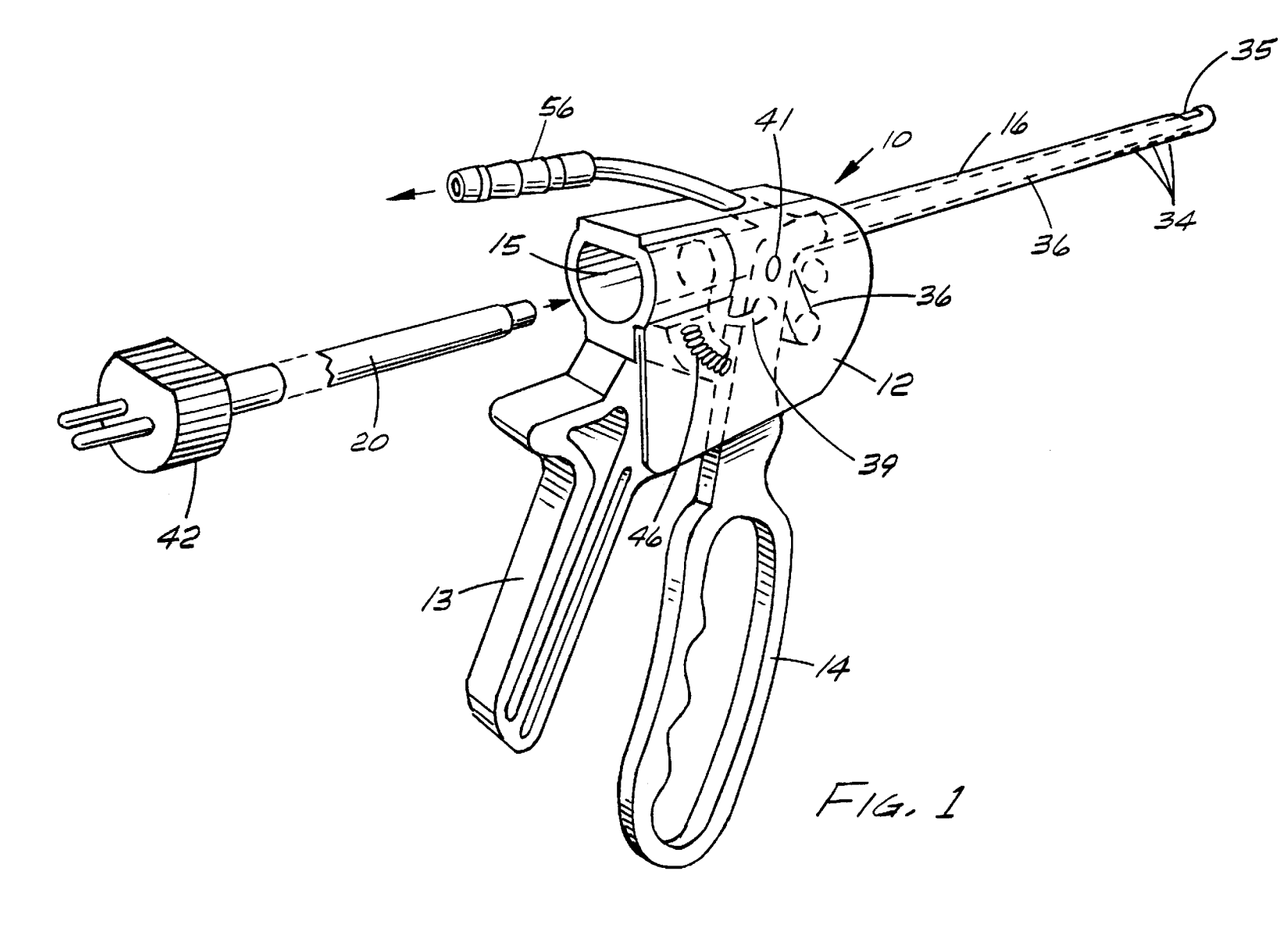
FIG. 1 is a perspective view of one form of an electrosurgical handpiece according to the invention fitted with a bipolar activator according to the invention and with the handle in its open position.

Referring now to FIG. 1, one form of bipolar handpiece according to the invention is shown at 10. It comprises a handle 12 having a grip 13, a trigger 14, and through a bore 15 at its top is mounted the outer first tubular member 16. The latter has a small outside diameter that will allow it to be inserted into the standard cannula used for MIS. A typical range is about 0.07–0.1 inches. A typical length is about 10–20 inches. The outer tubular member 16 is preferably supplied with an enlarged diameter end 18 (see FIG. 11) acting as a stop for the tubular member 16 when it is inserted into the handle bore 15 and secured therein by, for example, a set screw (not shown). This simple mounting allows the use of disposable assemblies of tubular member and electrodes if desired.

Figures 2, 3, 4:
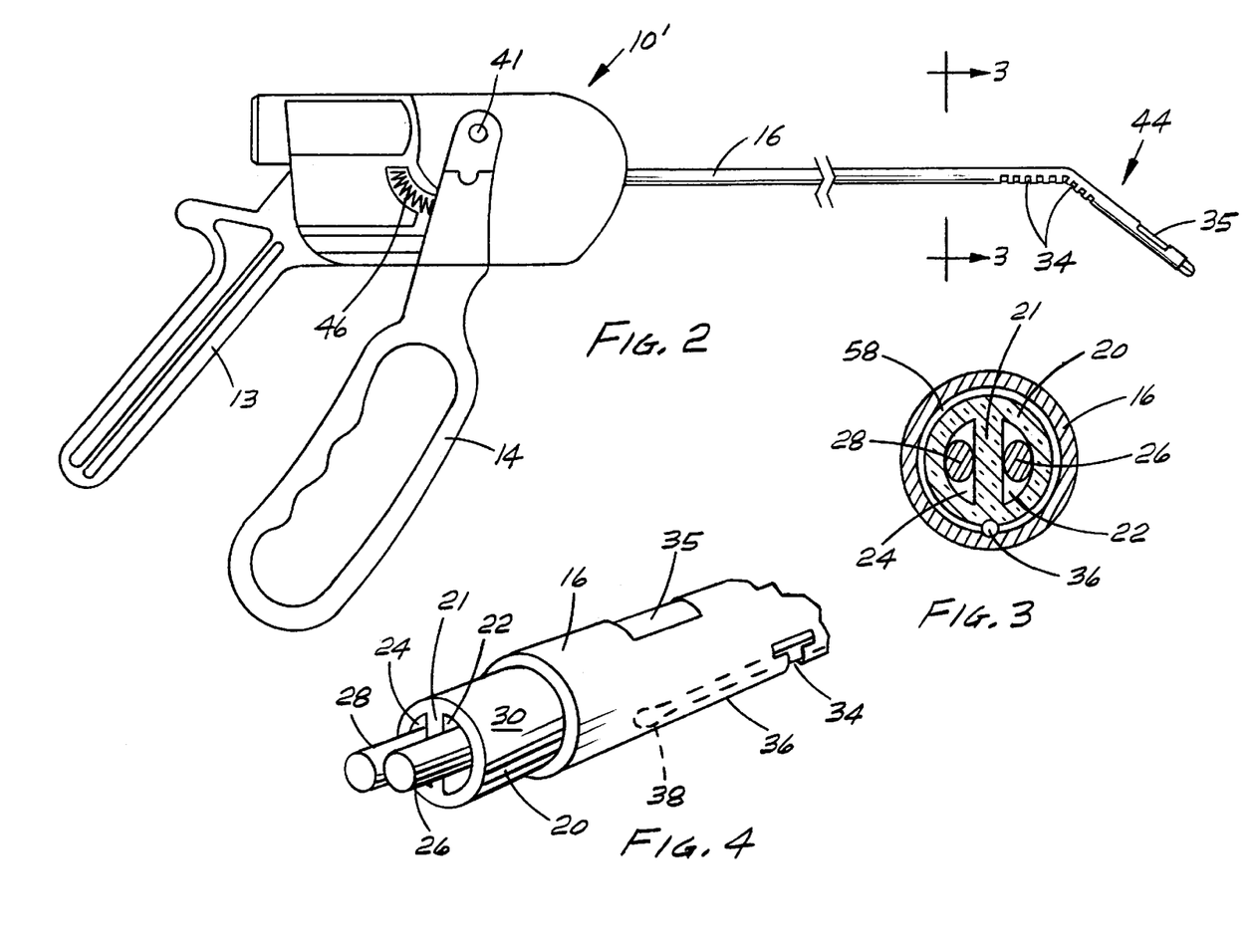
FIG. 2 is a side view of a variant of the handpiece of FIG. 1 with the handle in its closed position.
FIG. 3 is a cross sectional view of the handpiece of FIG. 2 along the line 3—3.
FIG. 4 partial perspective view of the working end of the electrosurgical handpiece of FIG. 2 illustrating an early step in its manufacture.
Figure 5:
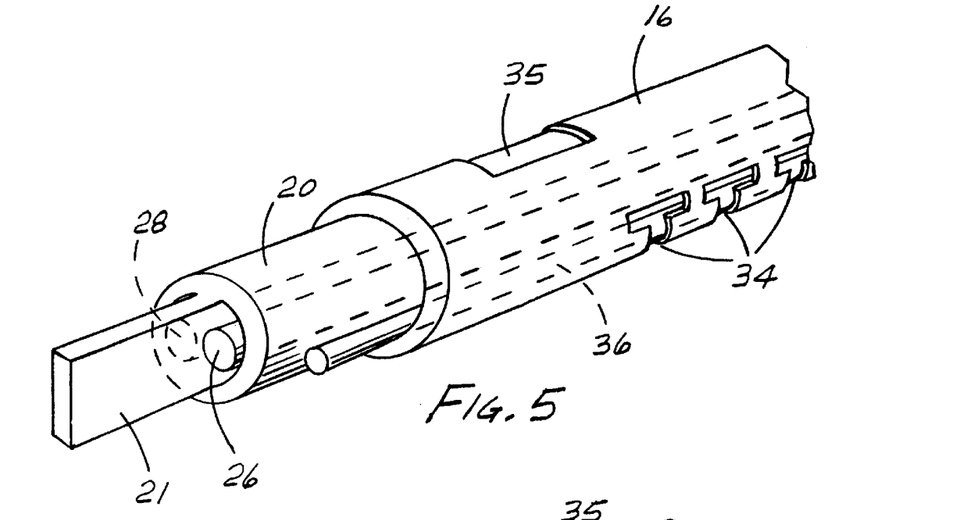
FIGS. 5 and 6 views similar to that of FIG. 4 illustrating later steps in its manufacture.

Inside the outer tubular member 16 is an inner electrically-insulating, for example, plastic, lumen (second tubular member) 20 that has an electrically-insulating wall 21 down its middle forming two electrically-insulated compartments 22, 24 (FIG. 3). The inner tubular member 20 may be secured within the outer tubular member 16 by any convenient means, such as a set screw (not shown), which, as will be explained in greater detail below, allows replacement of the second tubular member 20 with its bipolar electrode by a another bipolar electrode or a similarlyconfigured unipolar electrode. FIG. 1 illustrates this feature by showing an electrode 20 being plugged into the housing 12 via the opening 15 and extending into the outer tubular member 16. Two electrically-conductive wires 26, 28, for example of stainless steel, are each extended through one of the insulated compartments 22, 24, with the result that the wall 21 electrically separates the two conductive wires (FIG. 4). Additionally, the circular wall 30 surrounding the separating wall 21 for a short distance at the tube end is stripped back (FIG. 5) leaving only the separating wall 21 projecting forward. This projecting wall 21 now becomes the insulation between two half-ball electrodes 30, 32 connected as by welding to the projecting ends of the wires 26, 28 (FIG. 6).

Figures 6, 7:
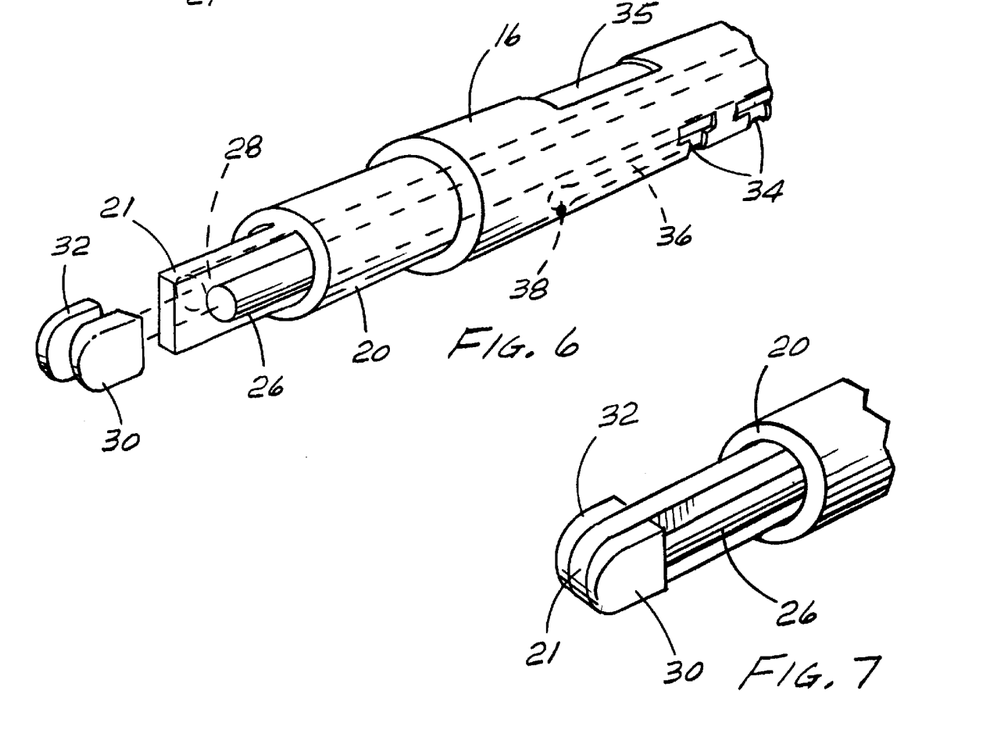
FIG. 7 shows the assembled end of the handpiece of FIG. 2.

FIG. 4 shows the remote end of the assembly before the half-ball electrodes have been added, and FIG. 6 shows the electrode wires 26, 28 which were first pulled forward to provide extra room to attach the half-ball electrodes 30, 32 to the wire ends, after which the wires are retracted pulling the half-ball electrodes back to their operative position, as shown in FIG. 7, in which the ball electrodes 30, 32 are fully spaced over their entire length (the direction of the longitudinal dimension of the assembly) by the center wall insulation 21.

The outer tubular member 16 is weakened at a location spaced a short distance from the remote end of the tubular member 16, as by cutting a series of spaced slots 34 that extend through the outer wall 30. A pull wire 36 is extended through the outer tubular member 16 along the bottom side of and outside of the inner tubular member 20, i.e., at the same side as the slots 34, and anchored 38 (FIG. 4) to the outer wall 30 as by use of adhesive or by fusion if the outer tubular member is of plastic, or by welding if the outer tubular member is of metal. An opening 35 is made in front of the slots 34 on the top part to provide access to the pull wire end to allow this connection to be made during assembly. The opposite end of the pull wire 36 is attached 39 to the trigger 14 (FIG. 1). The outer tubular member 16 is held in a stationery position within the handle 12, and the grip 13 is likewise stationery with respect to the handle 12. Hence, when the trigger 14, which is pivotably mounted 41 on the handle 12, is squeezed, illustrated in FIG. 2, the pull wire 36 to which it is attached applies a pulling force on the remote end of the outer tubular member 16 which as shown at 44 causes it to flex downward about the weakened section 34. When the trigger is released, the natural tendency of the outer tubular member 16 to return to its normal straight position restores it to the position shown in FIG. 1. If desired, a return spring 46 can be added to the trigger 14 to aid this motion.

Figures 8, 9, 10, 11:
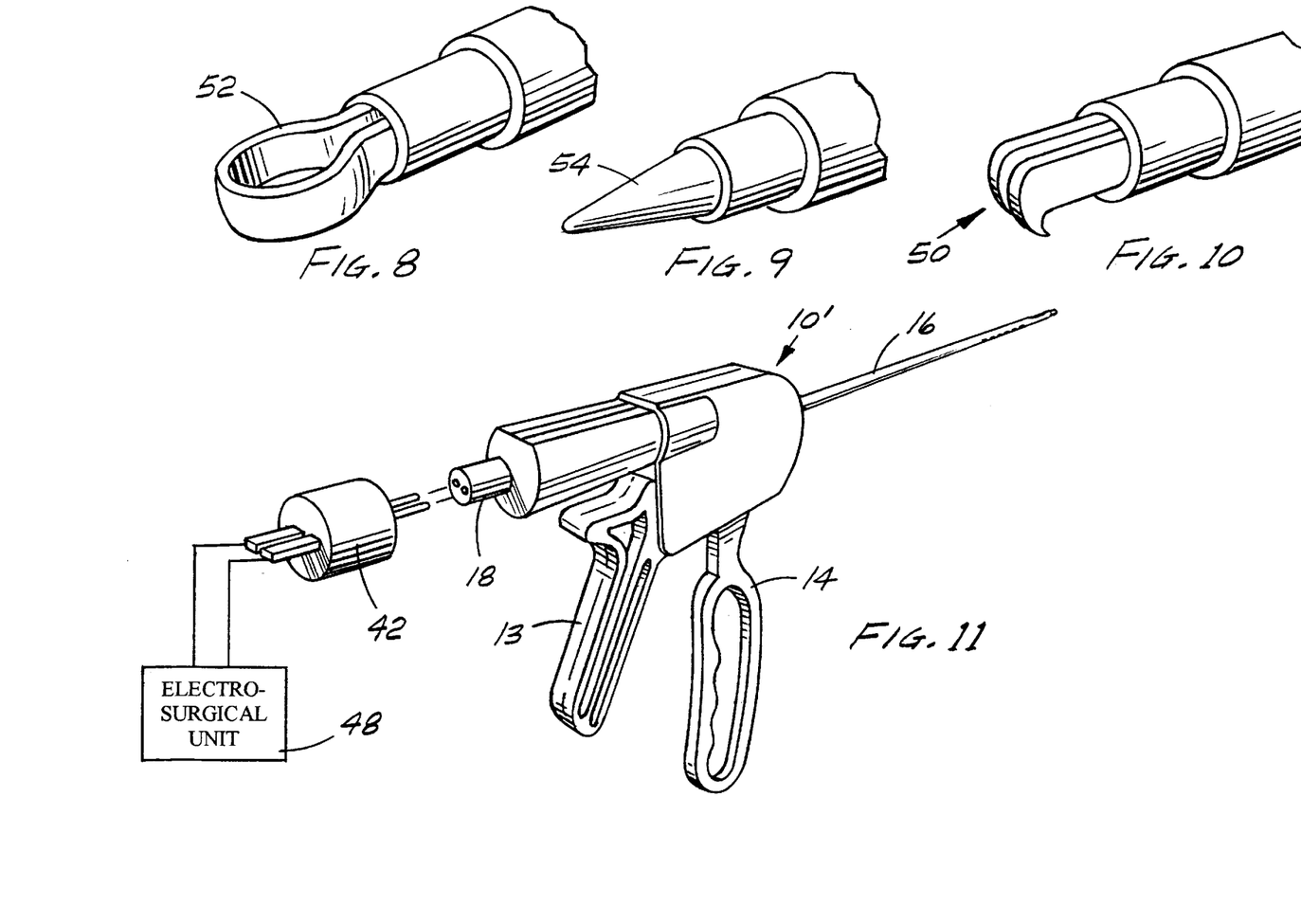
FIGS. 8 and 9 are views similar to that of FIG. 7 fitted with two kinds of unipolar activators according to the invention.
FIG. 10 is a view similar to that of FIG. 7 fitted with a different kind of bipolar activator.
FIG. 11 is a perspective view of the device of FIG. 7 shown connected to a bipolar adaptor and to an electrosurgical unit.

The inner tubular member 20 together with its insulated half-ball electrodes 30, 32 positioned at the end of this flexible tip is the actual bipolar electrode. Connected to the proximate ends of each of the wires 26, 28 is a standard bipolar connector 42 (FIG. 1). When the latter is plugged into a like connector on the front panel of a conventional electrosurgical unit, shown schematically at 48 (FIG. 11), and the unit activated, bipolar electrosurgical currents flow along the wires 26, 28 to the ball tips 30, 32 and an electrosurgical discharge is generated that extends between the ball electrodes 30, 32 around the end of the insulating wall separator 21. While it is preferred for reduction of herniated disks to use the ball electrodes, in a bipolar arrangement to confine the discharge to the immediate vicinity of the electrode ends, it will be understood that other known electrode shapes can be substituted for the ball electrodes, such as straight wires, needles, hooks, or loops. In addition, a feature of the invention is that the dual tubular member assembly makes it particularly easy to accommodate other electrode ends, by sliding out the inner tubular member 20 (see FIG. 1) from the outer tubular member 16 and sliding in its place another inner tubular member 20 with a different electrode configuration. This can be done before the outer tubular member 16 is extended through the cannula in the patient or even while the cannula is in place within the patient. In addition, a bipolar assembly in its dual lumen arrangement can be replaced by a unipolar electrode in a lumen with only a single compartment, in which case, the unipolar electrode end, with one of the aforementioned electrode shapes, would project forward from the end of the inner tubular member 20', which in this case would not require the center insulation present. This is illustrated in FIG. 9. When an electrode substitution is to be made, the surgeon can pull out the inner tubular member and replace it with another inner tubular member with a different electrode thereby enabling the surgeon to change electrodes during the procedure without removing the handle with its outer tubular member that has already been strategically placed in the surgical site. While a range of electrosurgical current frequencies can be employed, it is preferred that the frequency range employed be preferably in the range between 1.5 and 4 MHz.

FIGS. 8 and 10 illustrate other active electrode configurations. FIG. 10 shows a bipolar hook assembly 50, which can also easily be made unipolar. FIG. 8 shows a unipolar loop assembly 52. FIG. 9 shows a unipolar needle 54 or pointed electrode assembly.

Figure 12:
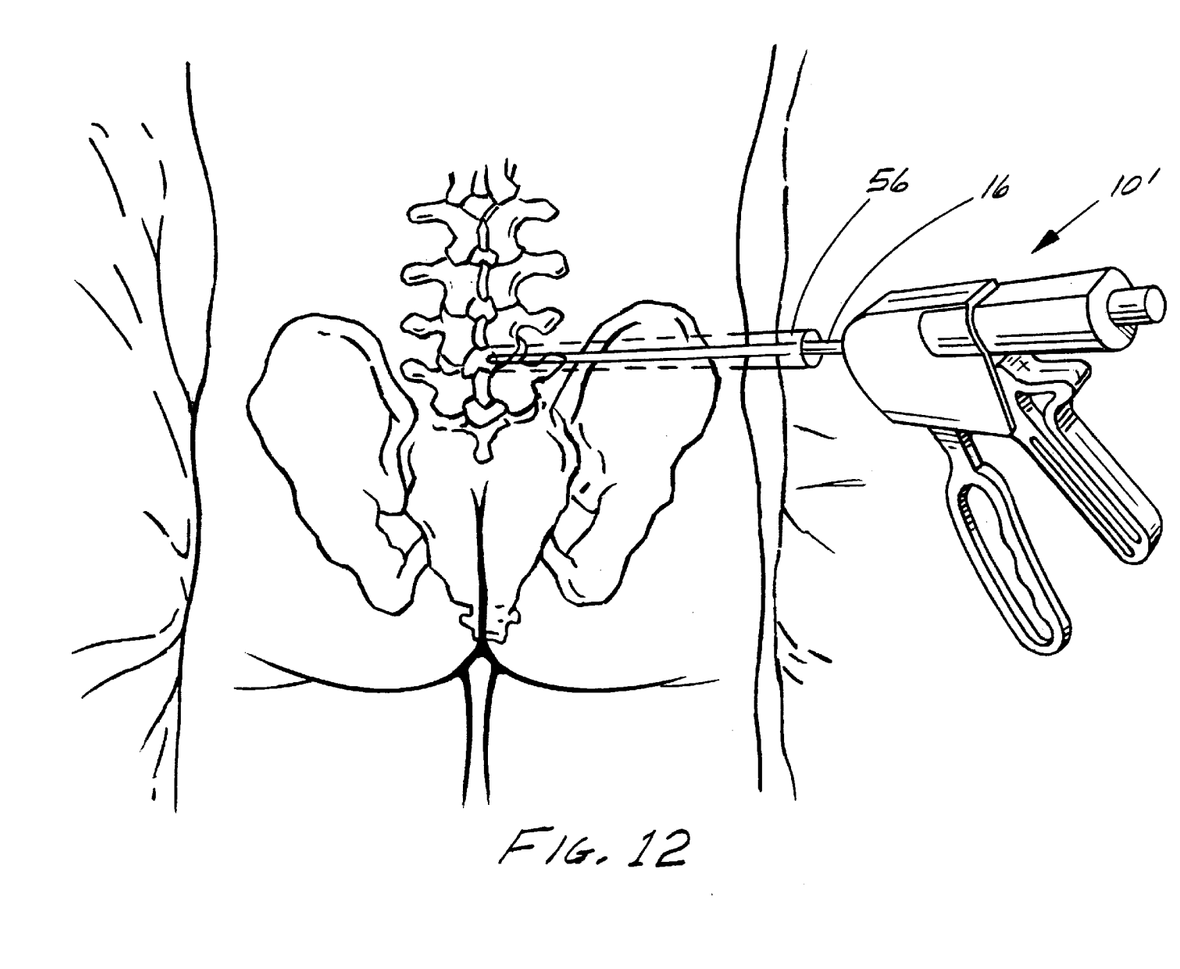
FIG. 12 illustrates use of the device of FIG. 11 in a laparoscopy procedure, namely, to reduce a herniated disk.

Among the benefits of this invention is that it offers the surgeon control and flexibility during surgeries that require difficult placement of electrodes and also movement of the active end at the active surgical area while the electrode is within the cannula to perform precision surgery. The degree to which the surgeon actually needs to bend the flexible tip depends upon its location relative to the disk area to be cut or shrunk. The flexible tip provides the surgeon with an additional degree of freedom in finding the optimum electrode position before energizing the electrosurgical unit. The long nozzle 16 is needed because, typically, the cannula 50 is inserted from the patient's side (FIG. 12), and the cannula 56 is positioned while the surgeon is observing the position of the cannula though the viewer. After the cannula is positioned properly, then the electrode 16 can itself be pushed through the cannula 56 until its flexible end 44 is outside the end of the cannula and further positioned within the disk surgical site by moving it forward or backwards and by flexing the electrode tip 44.

The connector 42 can be plugged directly into the electrosurgical mainframe 48, and thus the electrosurgical energy furnished at the electrode working end will be determined by the mainframe controls and a conventional footswitch. However, most surgeons prefer hand control of the electrosurgical energy, as was explained in the earlier referenced patent, which is easily accomplished by using the finger switch activator described in that earlier referenced patent and which can be mounted on the cannula or handle.

FIG. 1 shows a variant 10 in which the inner tubular member 20 is replaceable, and also is provided with a suction tube 56 connected to the handle and to the clearance space 58 (FIG. 3) between the inner and outer tubular members. When suction is provided at the end 56, it is delivered to the remote end of the outer tubular member 16 at the surgical site and thus will exhaust any fumes or smoke that may interfere with the surgeon's vision as well as cool the surgical site. The variant 10' of FIGS. 2 and 11 include a fixed inner tubular member 20 and lacks the suction feature.

While the parts of the electrosurgical handpiece, made up of metal and if of plastic, of Delrin for example, are autoclavable, the device is sufficiently simple that it can be manufactured at very low cost with a less expensive plastic and thus can be made disposable.

The handpiece of the invention is generally useful for treating tissue and is useful in particular in the following situations. Thermally induced radiofrequency for shrinkage of collagen, shrinkage and tissue denaturazation, and collagen contraction. For treating and producing profound shrinkage of capsular tissue, for example, due to denaturazation of collagen fibers. Also to shrink and remodel collagen fibrils after exposure to high frequency radiowave energy. As a further example, shrinkage of collagen to promote capsular stability has been shown to be effective for shoulder dislocations and herniated discs, as examples.

Figures 13, 14, 15:
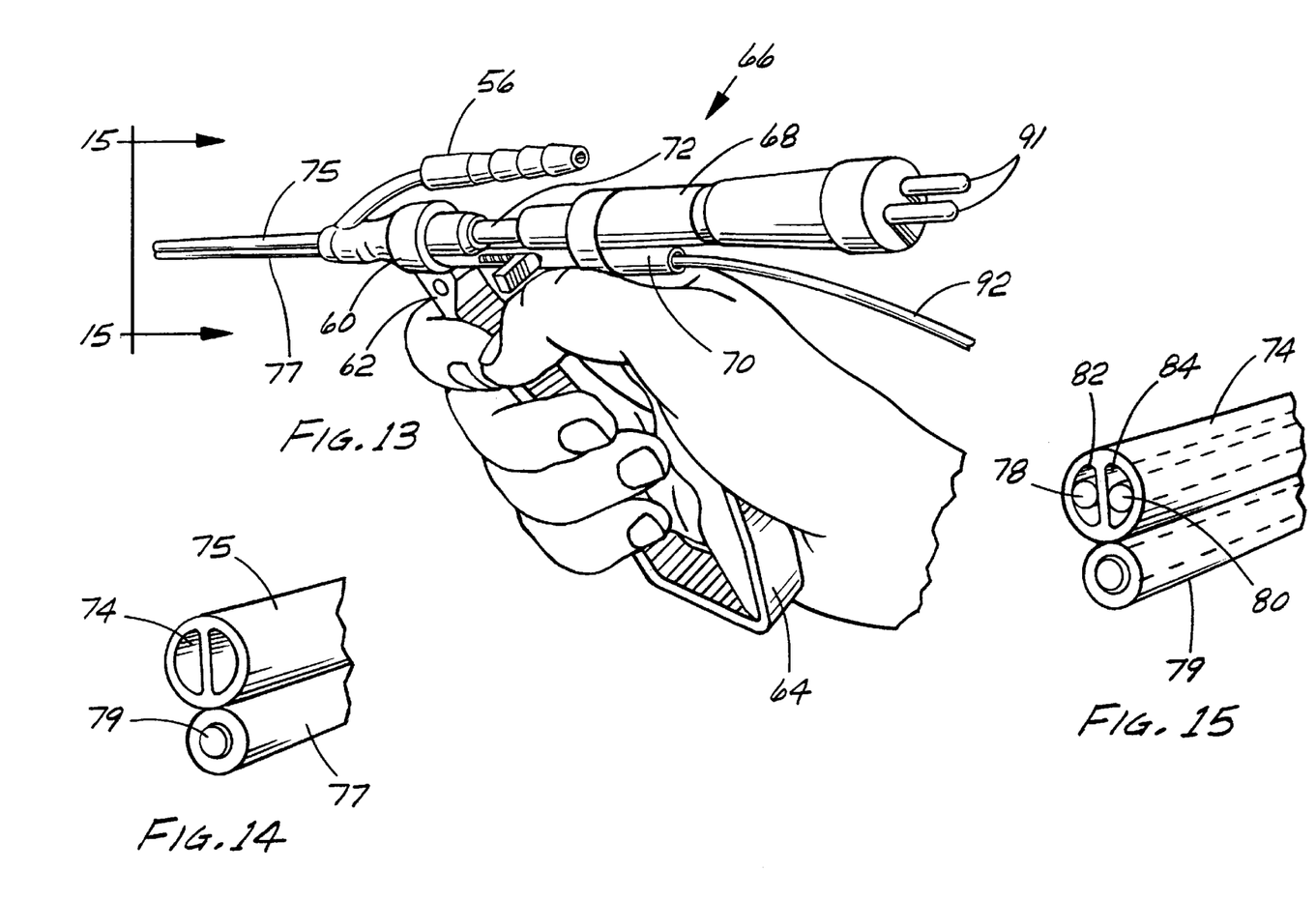
FIG. 13 is a perspective view of still another variant of a handpiece according to the invention comprising both a bipolar and a unipolar electrode.
FIG. 14 is an enlarged view of the working end of the handpiece of FIG. 13 with both electrodes in the retracted position.
FIG. 15 is a cross-sectional view along the line 15—15 of FIG. 13.

FIGS. 13–19 show a modification according to the invention comprising both a bipolar and a unipolar electrode, with the additional feature of allowing the surgeon to selectively choose and activate a bipolar or a unipolar electrode. This embodiment also includes as an additional feature electrodes with preconfigured ends such as pre-bent ends which are normally inside of a relatively stiff outer tube but which when extended outside of the outer tube will assume its pre-bent position. One form of this embodiment comprises a handle 60 to which is attached a hand grip having a forward portion 62 affixed to the handle 60 and a rearward portion 64 which is secured to a slidable stiff member 66 comprising an upper part 68 and a lower part 70. The upper part 68 is connected to a relatively stiff inner tube 72 which is slidable within the handle 60 and which is connected to and functions to push forward, when the grip is squeezed, a dual lumen 74 of the type illustrated in FIG., 7 together with its wires 78, 80 of a bipolar electrode 80 that may be of the half-ball type shown in FIG. 7 which extend through the dual compartments 82, 84 of the relatively stiff electrically-insulated inner first plastic tube 74. The latter is slidably mounted within a stiff outer tube 75. Below the latter is mounted a stiff second tube 77 which slidably houses a slidable electrically-insulated tube 79 housing a wire 81 connected at its end to an unipolar electrode 88. FIG. 15 shows just the two side-by-side electrically-insulated tubes 74 and 79 without the outer housings 75, 77.

Figures 16, 17:
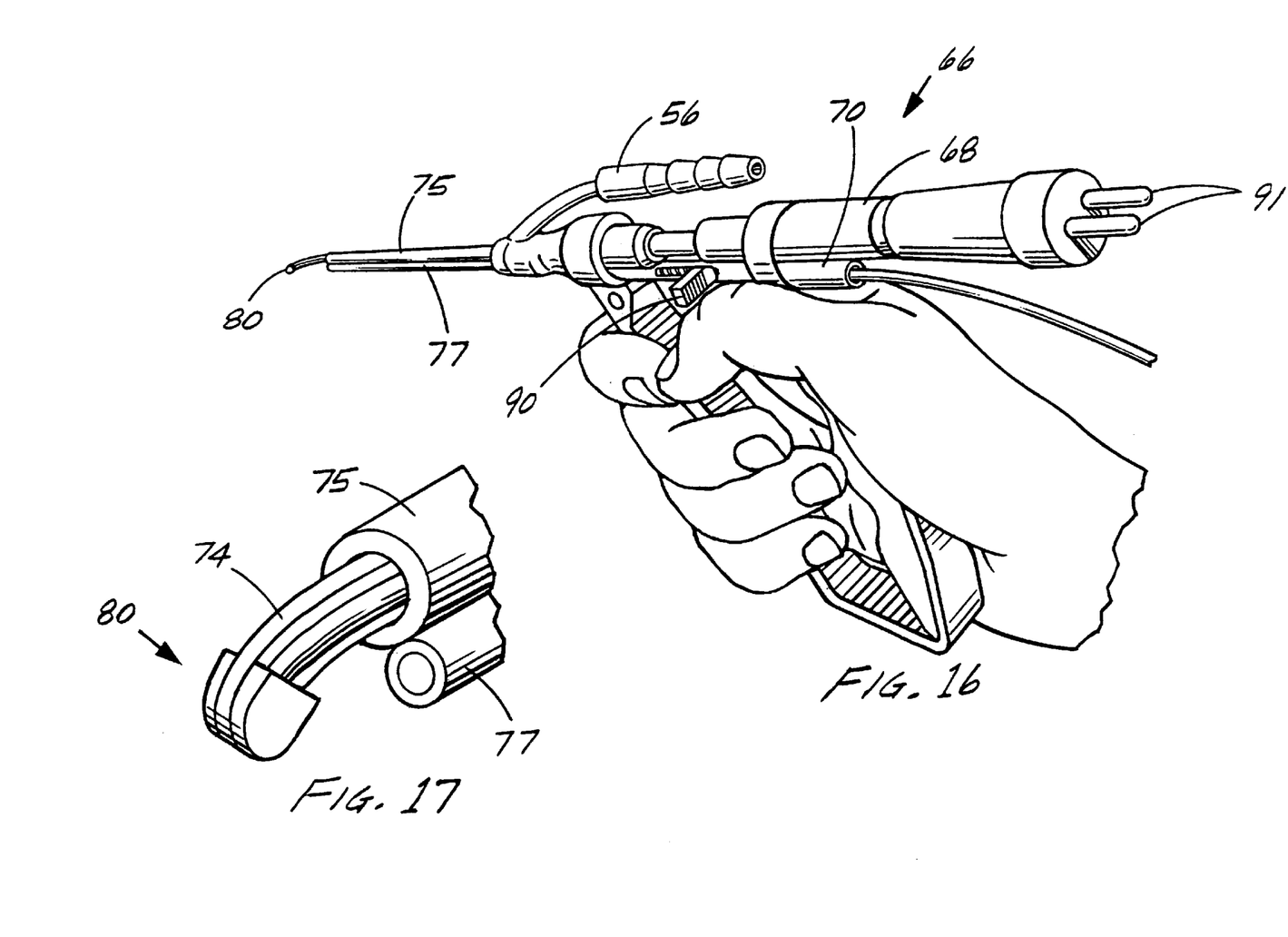
FIG. 16 is a perspective view of the handpiece of FIG. 13 with the bipolar electrode in its extended position and the unipolar electrode in its retracted position.
FIG. 17 is an enlarged view of the working end of the handpiece of FIG. 16.

Normally, both the bipolar and the unipolar electrodes are in their retracted position shown in FIGS. 13 and 14. When the grip is squeezed, the member 72 is pushed forward toward the working end causing the dual lumen 74 to which it is connected, together with its bipolar wires to which the bipolar electrode 80 is connected, to project forwardly out of their housing 74 as shown in FIGS. 16 and 17. The surgeon can then activate the electrosurgical unit to supply via terminals 91 bipolar electrosurgical currents to the bipolar electrode end 80. When the grip is released, the spring tension of the grip, or an additional spring (not shown) if needed, will cause the tube 74 to retract to the position shown in FIGS. 13 and 14. When it is desired to operate the unipolar electrode, the surgeon presses a slide 90 on the side of the tube 70, which slide is connected to the single tube 79, which causes it to move forwardly from its retracted position (FIG. 14) to its extended position shown in FIGS. 18 and 19. This action causes the unipolar electrode 88 to project forwardly. The surgeon can then activate the electrosurgical unit via wire 92 to supply unipolar electrosurgical currents to the unipolar electrode end 88. The two electrode movements are separate from one another so that the surgeon can selectively choose which electrode to use in the procedure. When the surgeon releases the slide 90, a spring (not shown) causes the single tube 79 to retract within its outer tube 77.

Figures 18, 19, 20:
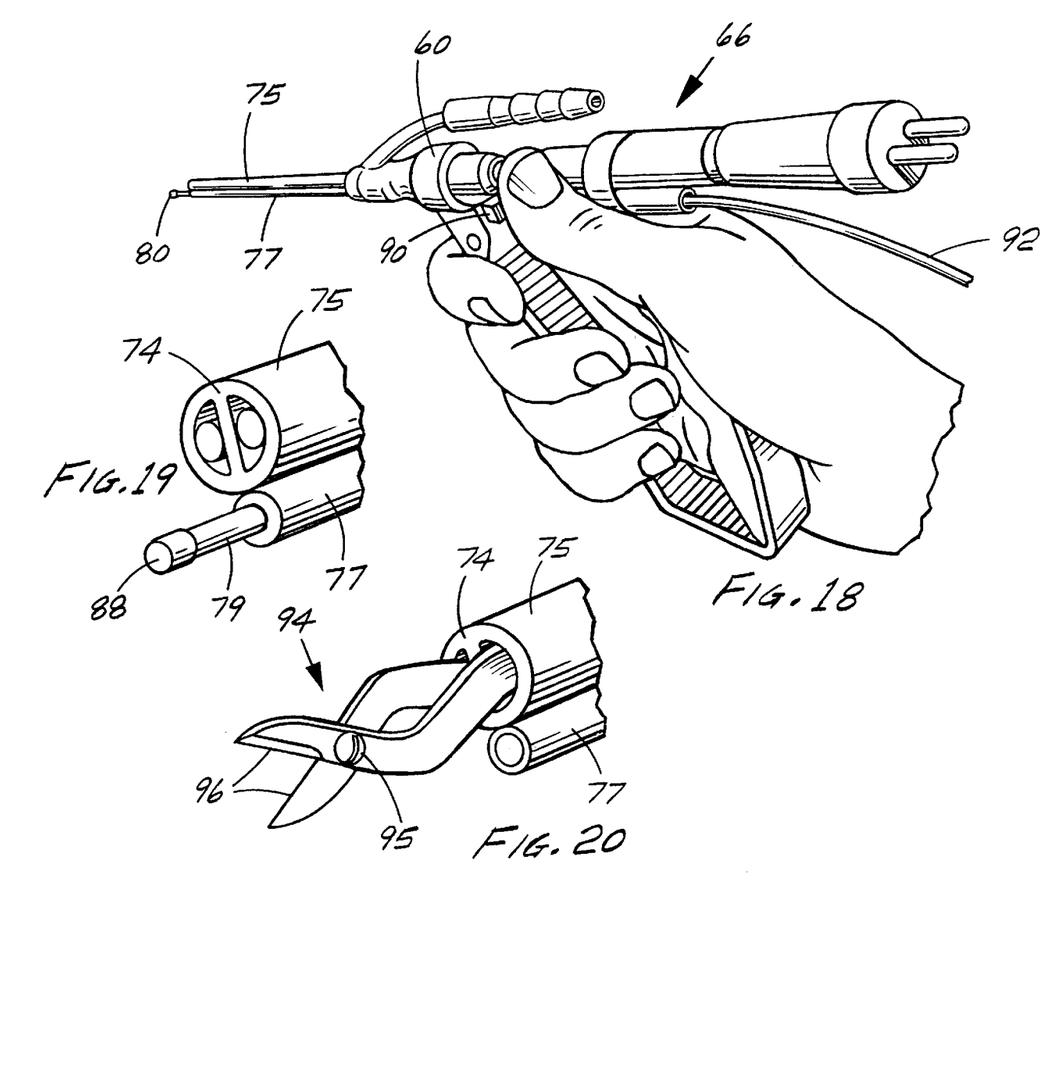
FIG. 18 is a perspective view of the handpiece of FIG. 13 with the unipolar electrode in its extended position and the bipolar electrode in its retracted position.
FIG. 19 is an enlarged view of the working end of the handpiece of FIG. 18.
FIG. 20 is an enlarged view of the working end of a handpiece of the type shown in FIG. 13 illustrating the use of a scissors embodiment.

Preferably, at least the projecting end of one, preferably both, of the respective bipolar/unipolar tube is made of a material that can be pre-bent and has sufficient memory to retain its pre-bent shape when extended outwardly from its restraining outer tube. Either a plastic can be used or a metal, such as stainless steel, which has been treated, as by tempering, to retain a pre-bent shape. This is well known in the art and suitable materials will be apparent to those in this art. If a metal is used for the inner tube, the electrode wires will have to be suitably insulated from one another or alternatively, the tube can be lined with an insulating layer. In this embodiment, with electrodes having a pre-bent and thus fixed shape, it is not possible to change their orientation, i.e., whether straight or the angle of the bending. The only control that the surgeon has is over the length of the extension. A feature of the invention is a family of unipolar and bipolar electrodes with differently-oriented ends, some bent in one direction, others bent is still other directions, and some straight. FIG. 17 shows one member of the family with an end that bends to the left. FIG. 19 shows a member of the family with an end that is straight. Typically, the family would contain either bipolar or unipolar electrodes or both with ends that are pre-bent in all four directions as well as straight. As in the FIG. 1 embodiment, new electrodes 74, 79 are easily plugged into the end of their respective tubular housing handle as needed, which can be done during the procedure. With the bipolar electrode, the replacement electrode telescopes through tube 68, so that when the latter is moved relative to grip 62, the entire tube 72 moves with it. With the unipolar electrode, as one example, the side can be provided with a rack (visible through the side slot in FIG. 13), with the slide 90 fitted with a suitable gear or other means to move the replacement tube 77 with the slide. The electrodes can be made at a relatively low cost and thus can be made disposable. The more expensive handle can be reused. Other handle constructions that allow extension and retraction of replaceable electrodes will be apparent to those skilled in this art.

Another example according to the invention of a replacement element for the bipolar or unipolar housing is shown in FIG. 20. In this case, the new structure is the same as that of FIG. 13 except that if desired the unipolar structure can be omitted. Only the working end is shown in FIG. 20, which in this embodiment is a scissors 94 comprising bent stainless steel scissor elements 96 connected at the gun end to the tube 72 and at the remote end connected by a pivot 95. As will be noted, the scissor elements 96 when extended out of their tube 75 are pre-configured to assume an open position. The grip 62, 64 (FIG. 13) is spring loaded so that the surgeon can extend the scissor elements 96 as shown by squeezing the grip. When the grip is released, the spring action causes the scissor elements to be retracted, the confining action of the walls of the tube 75 forcing the scissor ends together cutting in a normal scissor action any tissue around which the scissor ends have been placed. The dual lumen 74 allows bipolar currents to be applied to the scissor ends if desired, in which case the pivot 95 would have to electrically-insulate the two scissor elements, as with washers for example. The scissors 94 can also be configured for mounting in the unipolar tube 77 in which case unipolar currents can be applied to the scissor elements 96. It is also possible to have no terminals connected to the scissors 94 so that no electrosurgical currents can be applied thereto, in which case the scissors 94 can be operated just with a mechanical action. As before, the scissors 94 can have its own tubular housing 74 and thus be plugged into the gun of FIG. 13 to replace a bipolar or unipolar electrode, all while the tubular structure remains within the cannula during the procedure. It is preferred that the scissor end is pre-configured as in the FIG. 13 embodiment so that it can be caused to assume a particular orientation when extended, with the possibility of replacing it with a scissors of a different orientation if needed. Or if desired, it can be mounted as in the FIG. 1 embodiment with means for flexing the remote end of the structure. Other usable mechanical or electrical structures will be appreciated by those skilled in this art.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical bipolar handpiece comprising:
   (a) an elongated tubular first member having a first end and a remote flexible second end,
   (b) an elongated tubular second member located within the first member, said second member comprising an electrically-insulating tube having a first end and a remote flexible second end adjacent the first member's second end and comprising electrically-insulating means dividing the second tube into first and second compartments,
   (c) first and second electrically-conductive wires each positioned, respectively, in the first and second compartments and electrically-insulated from each other,
   (d) first means connected to the first member at its first end for applying electrosurgical bipolar currents to the first and second wires,
   (e) second means connected to the first member at its first end for selectively flexing the remote flexible end of the first member relative to the first end of the first member together with the remote flexible end of the second member, (f) active electrically-insulated electrosurgical electrodes connected to the first and second wires and extendable at the remote flexible end, said electrosurgical electrodes flexing together with the remote flexible ends when the second means is operated while maintaining them electrically-insulated.

2. An electrosurgical bipolar handpiece as claimed in claim 1, wherein the first member comprises a weakened section at its flexible end.

3. An electrosurgical bipolar handpiece as claimed in claim 2, wherein the weakened section comprises at least one slot in a side of the first member close to but spaced from the remote end of the first member.

4. An electrosurgical bipolar handpiece as claimed in claim 3, wherein the weakened section comprises a plurality of spaced slots.

5. An electrosurgical bipolar handpiece as claimed in claim 1, wherein the divider comprises an electrically-insulating wall portion which projects outwardly from the remote end of the second member, the electrodes being positioned on opposite sides of the projecting wall portion.

6. An electrosurgical bipolar handpiece as claimed in claim 1, wherein the second means comprises a pull wire or string positioned inside of the first member and connected at one end to the remote end of the first member, further comprising means for pulling the other end of the pull wire or string.

7. An electrosurgical bipolar handpiece as claimed in claim 1, wherein the first member has a length of about 10–20 inches and a diameter between about 0.07–0.1 inches for insertion into an minimally-invasive surgery cannula.

8. An electrosurgical bipolar handpiece as claimed in claim 1, wherein the active electrically-insulated electrodes comprise half-ball electrodes.

9. An electrosurgical bipolar handpiece as claimed in claim 8, wherein the half-ball electrodes are laterally separated such that their facing sides are flat.

10. A procedure for surgically treating tissue comprising:

(I) providing an electrosurgical handpiece comprising:
  (a) an elongated tubular first member having a first end and a remote flexible second end,
  (b) an elongated tubular second member located within the first member, said second member comprising an electrically-insulating tube having a first end and a remote flexible second end adjacent the first member's second end and containing an electrically-insulating divider dividing the second tube into first and second compartments,
  (c) first and second electrically-conductive wires each positioned, respectively, in the first and second compartments and electrically-insulated from each other,
  (d) first means connected to the first member at its first end for applying electrosurgical bipolar currents to the first and second wires,
  (e) second means connected to the first member at its first end for selectively flexing the remote flexible end of the first member relative to the first end of the first member together with the remote flexible end of the second member,
  (f) active electrically-insulated electrosurgical electrodes connected to the first and second wires and selectively extendable out of their respective compartments at the remote flexible end, said electrosurgical electrodes flexing together with the remote flexible ends when the second means is operated while maintaining them electrically-insulated, (II) inserting the first tubular member into a patient in the vicinity of tissue to be treated, (III) flexing the remote flexible end to position the electrosurgical electrodes at the tissue to be treated, (IV) applying electrosurgical currents to the first end to provide a bipolar discharge to generate heat at and treat the tissue.

11. A procedure for surgically shrinking tissue as set forth in claim 10, wherein a cannula is first inserted into the patient and the first tubular member is then inserted into the cannula until its flexible end is adjacent the tissue, after step (IV), the second tubular member is removed from the first tubular member and replaced by another second tubular member with a different electrode configuration without removing the first tubular member from the cannula, and then the electrode in the other second tubular member is energized.

12. A procedure for surgically shrinking tissue as set forth in claim 10, wherein clearance for gas flow is provided between the first and second members, and suction is applied to the clearance.

13. A procedure for surgically shrinking tissue as set forth in claim 11, wherein the electrosurgical handpiece is provided with a unipolar electrode and means for selectively making accessible at the remote end one of the bipolar and unipolar electrodes and for selectively energizing same, further comprising the step of first treating the tissue with one of the bipolar and unipolar electrodes and then treating the tissue with the other of the bipolar and unipolar electrodes while the first tubular member remains within the cannula.

* * * * *